United States Patent
Kubota et al.

(10) Patent No.: US 6,677,985 B1
(45) Date of Patent: Jan. 13, 2004

(54) ULTRASONIC VIDEO APPARATUS

(75) Inventors: Jun Kubota, Nagareyama (JP); Ryuichi Shinomura, Higashimatsuyama (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/601,615

(22) PCT Filed: Mar. 5, 1999

(86) PCT No.: PCT/JP99/01076

§ 371 (c)(1),
(2), (4) Date: Aug. 4, 2000

(87) PCT Pub. No.: WO99/44504

PCT Pub. Date: Sep. 10, 1999

(30) Foreign Application Priority Data

Mar. 6, 1998 (JP) .......................... 10-055157

(51) Int. Cl.[7] .......................... H04N 7/18; G01S 15/89; A61B 8/00; A61B 8/02
(52) U.S. Cl. .......................... 348/77; 348/163; 600/441; 600/453; 600/454
(58) Field of Search .......................... 348/61, 64, 77, 348/163, 162; 382/128, 137; 128/915–916; 600/437, 441, 443, 453, 454, 455, 463, 465, 472

(56) References Cited

U.S. PATENT DOCUMENTS

| | | | | |
|---|---|---|---|---|
| 4,141,347 A | * | 2/1979 | Green et al. | 600/441 |
| 4,690,150 A | * | 9/1987 | Mayo, Jr. | 600/440 |
| 4,729,019 A | * | 3/1988 | Rouvrais | 348/163 |
| 4,865,040 A | * | 9/1989 | Ogasawara | 600/450 |
| 5,058,593 A | * | 10/1991 | Forestieri et al. | 600/453 |
| 5,083,566 A | * | 1/1992 | Baba | 600/441 |
| 5,123,417 A | * | 6/1992 | Walker et al. | 600/455 |
| 5,148,809 A | * | 9/1992 | Biegeleisen-Knight et al. | 600/443 |
| 5,224,175 A | * | 6/1993 | Gouge et al. | 382/128 |
| 5,241,473 A | * | 8/1993 | Ishihara et al. | 600/443 |
| RE35,148 E | * | 1/1996 | Lizzi et al. | 348/163 |
| 5,977,538 A | * | 11/1999 | Unger et al. | 250/227.2 |

OTHER PUBLICATIONS

Kulkarni et al., "Velocity accuracy enhancement and frame rate limitations in color Doppler optical coherence tomography", Conference on Technical Digest, Lasers and Electro–Optics, IEEE, pp. 125–127, May 1998.*

* cited by examiner

Primary Examiner—Vu Le
(74) Attorney, Agent, or Firm—Antonelli, Terry, Stout & Kraus, LLP

(57) ABSTRACT

An ultrasonic imaging apparatus having a depth range setter 28 for setting a threshold value of detection level for a Doppler signal in an ultrasonic circuit unit 2, a unit for extracting a time at which the Doppler signal exceeds the set detection level and a signal level in excess of the set detection level, and a ROI depth data generator 29 for determining, for an adaptive phase controller 3, a ROI depth range for correction necessary to make echo signals of neighboring channels be in phase by using the extracted time and signal level, whereby the focal point can follow the ROI region in an object to be inspected by correcting echo signals from the region where the intensity of the Doppler signal reaches the detection level or its neighboring region so as to make them be in phase between adjacent transducers.

17 Claims, 7 Drawing Sheets

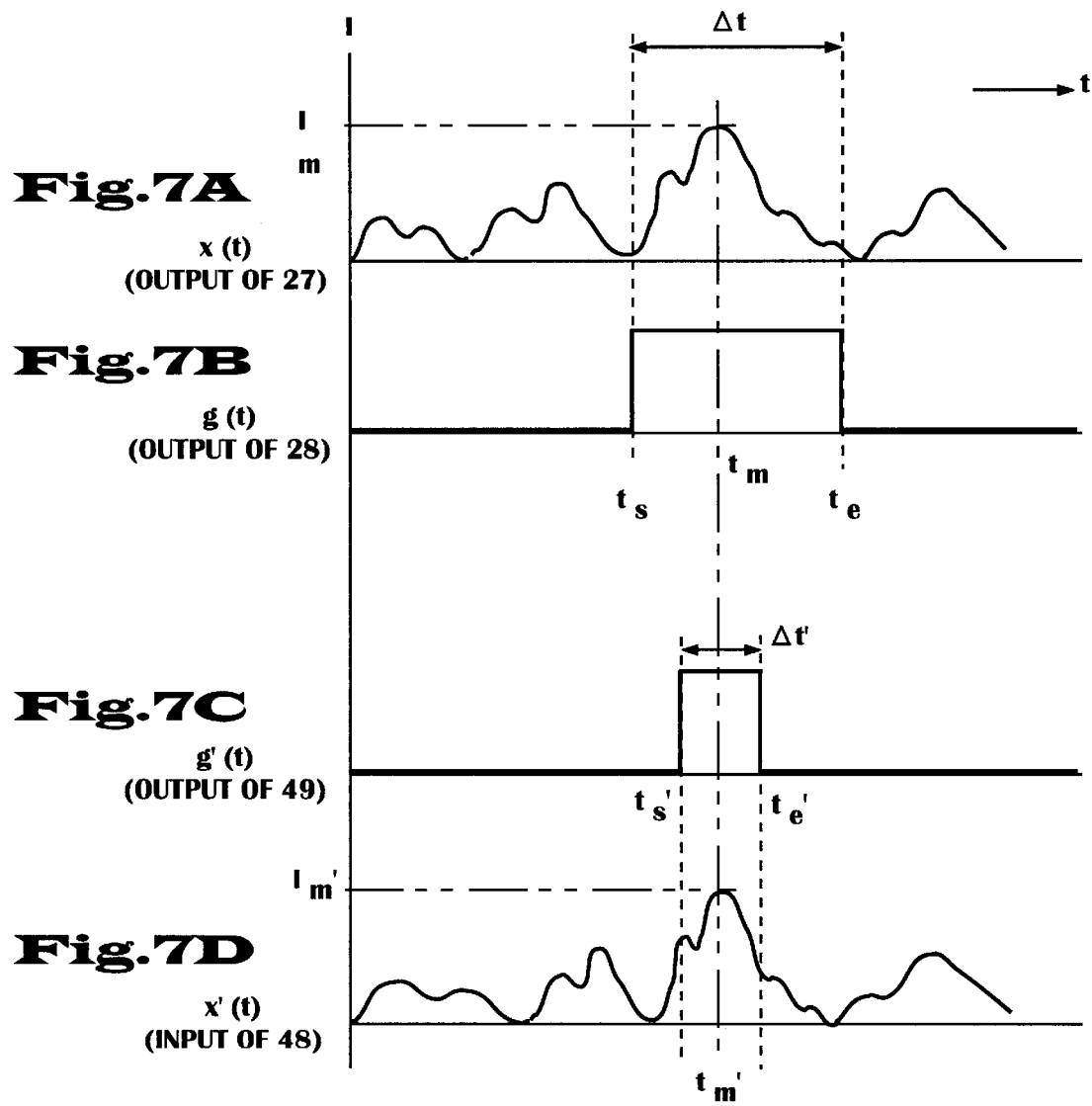

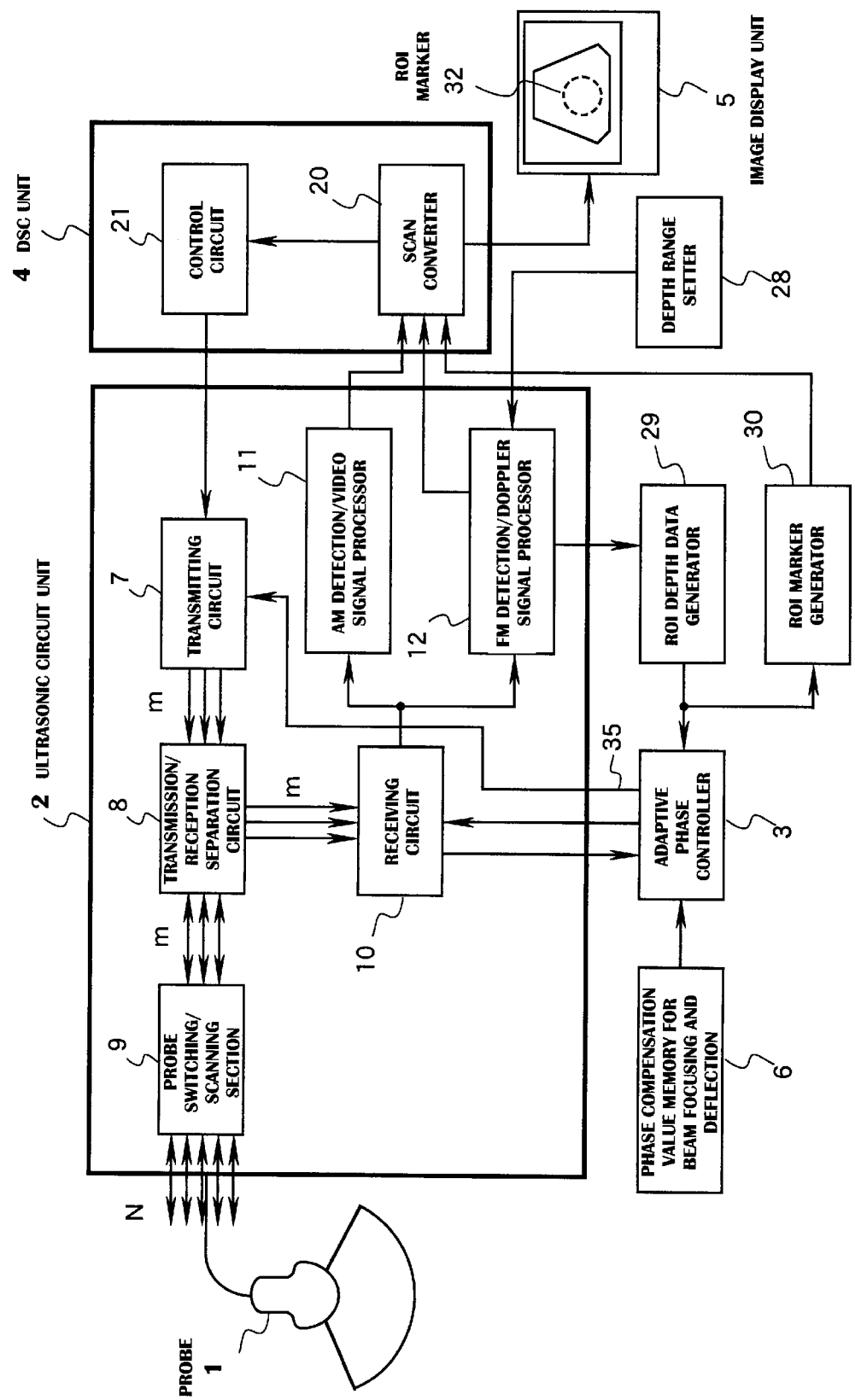

ULTRASONIC VIDEO APPARATUS

TECHNICAL FIELD

The present invention relates to an ultrasonic imaging (video) apparatus for transmitting ultrasonic waves to a diagnostic region in an object to be inspected and receiving reflected echoes to obtain and display an ultrasonic tomographic image and a Doppler image of the diagnostic region and more particularly, to an ultrasonic imaging apparatus of adaptive imaging type which can automatically make focus on a moving reflection region desired to be really inspected (ROI region) by monitoring signals indicative of movement and flow in an ultrasonic beam and adaptively making receiving signals developing at the depth (distance between a probe and the signal reflector) be in phase and which can display an adaptive image targeted to only the moving reflection region (moving target) on substantially real time base.

BACKGROUND ART

In a conventional ultrasonic imaging apparatus of adaptive imaging type, an ultrasonic beam is formed by electronically controlling circuit characteristics such that phases of transmission/reception signals from/to an array of fine ultrasonic transducers are referenced to a reflected echo signal of high intensity from a living body and reflected echo signal waveforms received by neighboring transducers in the array are made to be in phase and the ultrasonic beam is scanned to image the distribution of acoustic impedances due to structures in the body, the distribution of flow speeds of humors or movements of internal organ or the temporal changes of these quantities.

In the above conventional adaptive imaging type ultrasonic imaging apparatus, however, the ultrasonic image to be displayed is handled in a general manner and adaptive imaging is carried out by correcting phase data without discriminating which region the image belongs to. In this case, since in the ultrasonic image a reflected echo signal from a diagnostic region has, in general, its intensity which is often medium or rather low, focusing cannot be made on a region desired to be observed by an inspector, especially a moving region of interest (ROI) (moving reflection region). Accordingly, focusing is not made on movement of the diagnostic region or a flowing ROI region and its image becomes blurred, thereby failing to provide an excellent diagnostic image.

DISCLOSURE OF INVENTION

Accordingly, an object of the present invention is to provide an ultrasonic imaging apparatus which can deal with the problems as above and which can automatically make focus on a ROI region (moving reflection region) desired to be really inspected by monitoring signals indicative of movement and flow in an ultrasonic beam and adaptively making receiving signals developing at the depth be in phase.

Another object of the invention is to provide an ultrasonic imaging apparatus which can display an adaptive image targeted to only the moving reflection region on substantially real time base.

To accomplish the above objects, an ultrasonic imaging apparatus according to the present invention comprises a unit for transmitting ultrasonic beams in a predetermined direction having a moving internal organ in an object to be inspected or blood flow, a unit for receiving reflected echo signals affected by the Doppler effect due to the moving internal organ or blood flow and a unit for detecting a region in which the moving internal organ or blood flow exists from the received reflected echo signals, and image the distribution of irregularities of acoustic characteristics due to body tissues in the object to be inspected and the moving internal organ or blood flow as ultrasonic images, wherein the reflected echo signals from the region in the object to be inspected where the presence of the moving internal organ or blood flow is detected are used to compensate irregularities of acoustic characteristics of body tissues in the object to be inspected so that delay data for adaptive imaging necessary to make ultrasonic waves be in phase at the detection region at adjacent transducers on an ultrasonic probe may be determined, and the ultrasonic transmission/reception is carried out by using the thus determined delay data to perform adaptive image processing.

The delay data for adaptive imaging may be determined in respect of an ultrasonic beam for a given location and immediately after transmission/reception of the above ultrasonic beam, the ultrasonic transmission/reception for the same location may be effected in the same beam direction by using the thus determined delay data.

In this case, the frame rate is decreased by performing the adaptive process but a substantially accurate adaptive process can be effected for the beam.

Further, the delay data for adaptive imaging may be determined in respect of an ultrasonic beams for a given location and the ultrasonic transmission/reception may be effected for a location adjacent to the ultrasonic beam or in the adjacent beam direction by using the thus determined delay data.

In this case, there results an approximate accuracy because the process is not for the same beam but the process can be performed without degrading the frame rate.

Furthermore, the delay data for adaptive imaging may be determined in respect of all ultrasonic beams in a given frame and the ultrasonic transmission/reception may be carried out in the overall beam directions in the next frame by using the thus determined delay data.

In this case, the adaptive process is reflected every frame but each frame can be formed within the same time as that for an instance devoid of the process and therefore a similar image can be formed for movement of the object to be inspected.

Further, the delay data for adaptive imaging may be determined in respect of all ultrasonic beams in a given frame, the thus determined delay data for all ultrasonic beams may be stored together with corresponding ultrasonic beam waveforms by making correspondence of the delay data with the ultrasonic beam waveforms and the beams may be formed by adding the corresponding ultrasonic beam waveforms while compensating them for delay by using the stored delay data.

In this case, the circuit scale is increased but a really accurate adaptive process can be carried out without degrading the frame rate.

Further, in an ultrasonic imaging apparatus relevant to the above invention comprising a probe having an array of a plurality of transducers and being operative to transmit/receive ultrasonic waves to/from an object to be inspected, an ultrasonic circuit unit for supplying transmitting pulses to the probe to generate ultrasonic beams, adding reflected echo signals received by the probe while making them be in phase, processing a beamformed echo signal to deliver it as a tomographic image signal and detecting and delivering a Doppler signal by removing a fundamental wave from the beamformed echo signal through a filter, a phase controller for correcting the reflected echo signals in the ultrasonic circuit unit such that echo signals of neighboring channels are made to be in phase, a digital scan converter unit for performing scan conversion by writing and reading the reflected echo signals from the ultrasonic circuit unit to and from a memory and an image display unit for displaying image data from the digital scan converter unit as an ultrasonic image, there are provided a unit for setting a threshold value of detection level for the Doppler signal in the ultrasonic circuit unit, a unit for extracting a time at which the Doppler signal exceeds the set detection level and a signal level in excess of the set detection level, and a unit for determining, in said phase controller, a ROI depth range for correction necessary to make echo signals of adjacent channels be in phase by using the extracted time and signal level, whereby the focal point can follow the ROI region in the object to be inspected by correcting echo signals from the region where the intensity of the Doppler signal reaches the detection level or its neighboring region so as to make them be in phase between adjacent transducers.

Besides, there is provided a unit for fetching a signal from the unit for determining the ROI depth range and generating a signal for displaying a marker at a position corresponding to the depth range on the image display unit, whereby the marker is displayed at the ROI region in the object to be inspected which the focal point follows.

FIG. 1 is an explanatory diagram showing an outline of operation when the ultrasonic imaging apparatus having the above individual units is applied to a convex scanning format. In FIG. 1, given that a contour 37 of an internal organ exists within a range of frame of a convex scanning area 36 and a blood vessel 38 is inside the contour, it is assumed that an ultrasonic beam 39 passes through the contour 37 of internal organ and the blood vessel 38 at a moment. On the assumption that the contour 37 of internal organ and blood vessel 38 move at the next moment as shown at reference numerals 37' and 38', a Doppler shift signal due to the movement is detected and adaptive focusing processing is applied to reflected echo signals from a neighboring structure (wall of the internal organ or wall of the blood vessel) on the basis of the detected Doppler shift signal. This is a feature of the present invention.

Besides, FIG. 2 is an explanatory diagram showing an outline of operation when the ultrasonic imaging apparatus having the above individual units is applied to a linear scanning format. In FIG. 2, it is assumed that a front wall 42 of a blood vessel 41 is within a range of frame of a linear scanning area 40 and a blood flow 43 passes through the blood vessel. It is then assumed that an ultrasonic beam 44 passes through the front wall 42 of blood vessel 41 and the blood flow 43. In this state, a Doppler shift signal generated from the blood flow 43 is detected and adaptive focusing processing (adaptive image process) is applied to reflected echo signals from its neighboring structure (the aforementioned blood vessel wall) on the basis of the detected Doppler shift signal. This is another feature of the present invention.

BRIEF DESCRIPTION OF DRAWINGS

FIGS. 7A, 7B, 7C and 7D are diagrams for explaining the operation of maximal search circuits added in the present invention.

FIG. 8 is a block diagram of another embodiment of the ultrasonic imaging apparatus according to the invention.

BEST MODE FOR CARRYING OUT THE INVENTION

Embodiments of the present invention will be described hereunder with reference to the accompanying drawings.

Figure 1:
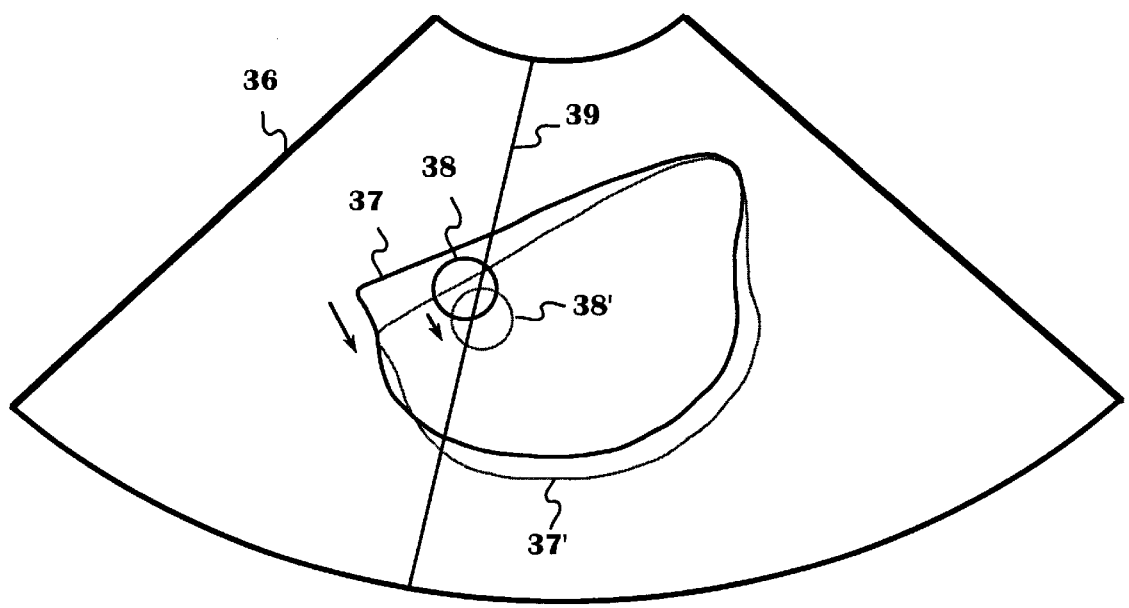
FIG. 1 is an explanatory diagram showing an outline of operation when the ultrasonic imaging apparatus according to the present invention is applied to a convex scanning format.
Figure 2:
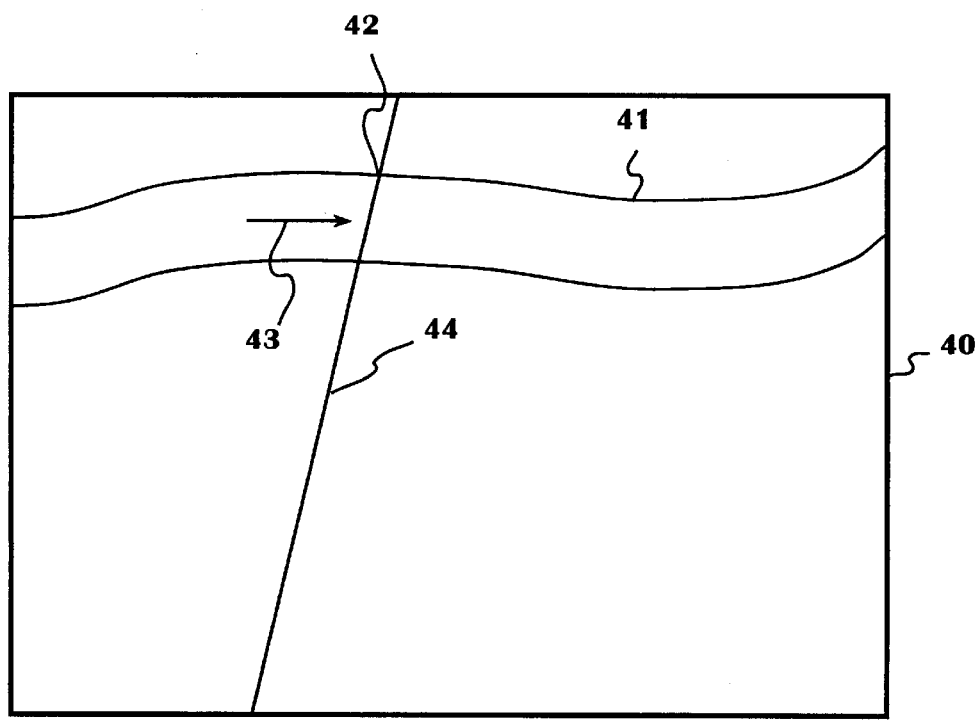
FIG. 2 is an explanatory diagram showing an outline of operation when the ultrasonic imaging apparatus according to the present invention is applied to a linear scanning format.
Figure 3:
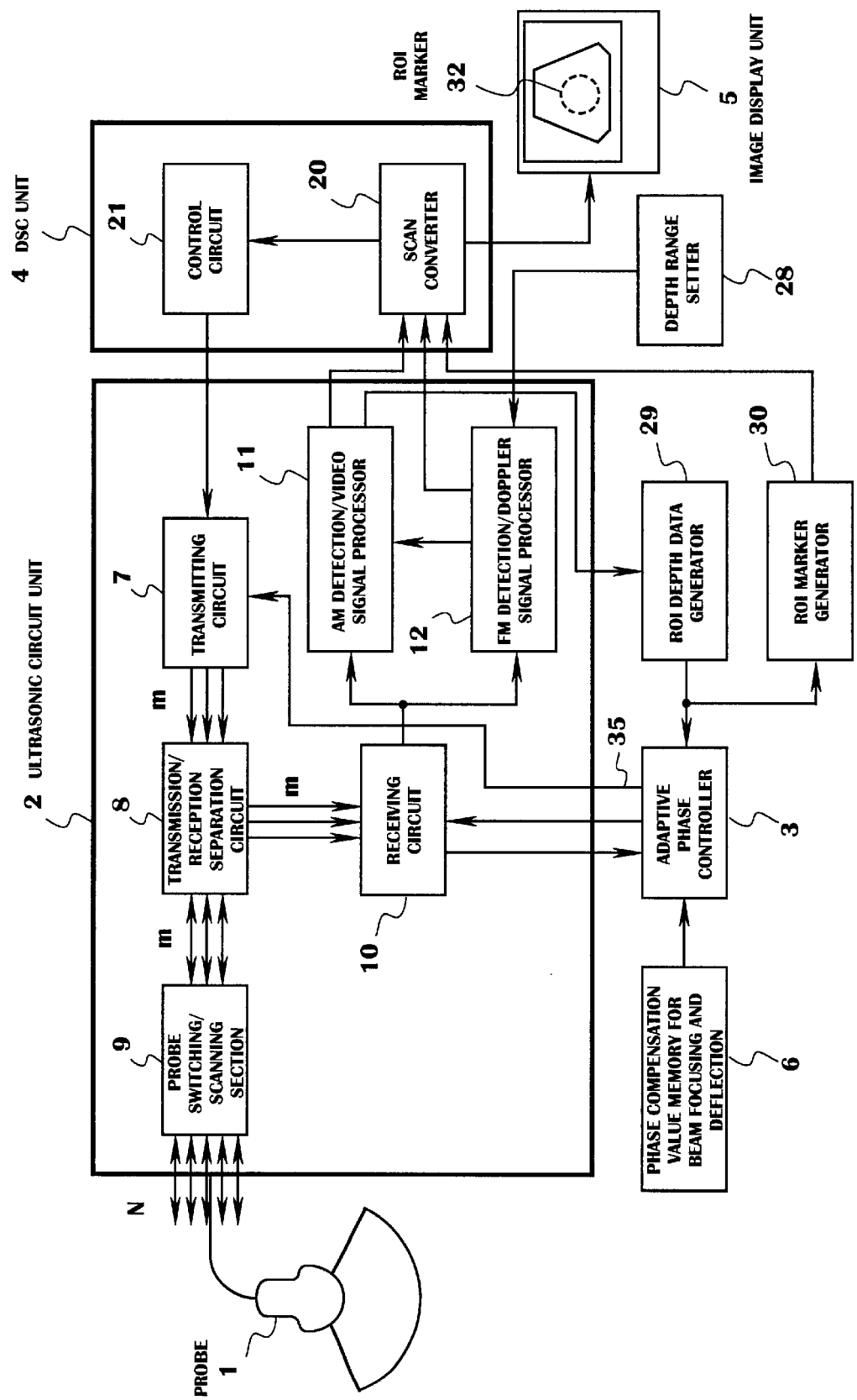
FIG. 3 is a block diagram showing an embodiment of the ultrasonic imaging apparatus according to the invention.

FIG. 3 is a block diagram showing an embodiment of an ultrasonic imaging apparatus according to the invention. The ultrasonic imaging apparatus transmits ultrasonic waves to a diagnostic region in an object to be inspected and receives reflected echoes to obtain and display an ultrasonic tomographic image and a Doppler image of the diagnostic region. Especially, the apparatus is of the adaptive imaging type and has, as shown in FIG. 3, a probe 1, an ultrasonic circuit unit 2, an adaptive phase controller 3, a DSC unit 4, an image display unit 5 and a phase compensation value memory 6 for beam focusing and deflection and further comprises a depth range setter 28, a ROI depth data generator 29 and a ROI marker generator 30.

The probe 1 has a plurality of transducers arranged in an array form and transmits/receives ultrasonic waves to/from the object to be inspected. The ultrasonic circuit unit 2 supplies transmitting pulses to the probe 1 to generate ultrasonic beams, adds reflected echo signals received by the probe 1 while making them be in phase and processes a beamformed echo signal to deliver a tomographic image signal and besides, it removes a fundamental wave from the beamformed echo signal through a filter to detect and deliver a Doppler signal. Internally, the ultrasonic circuit unit has a transmitting circuit 7, a transmission/reception separation circuit 8, a probe switching/scanning section 9, a receiving circuit 10, an AM detection/video signal processor 11 and an FM detection/Doppler signal processor 12.

Figure 4:
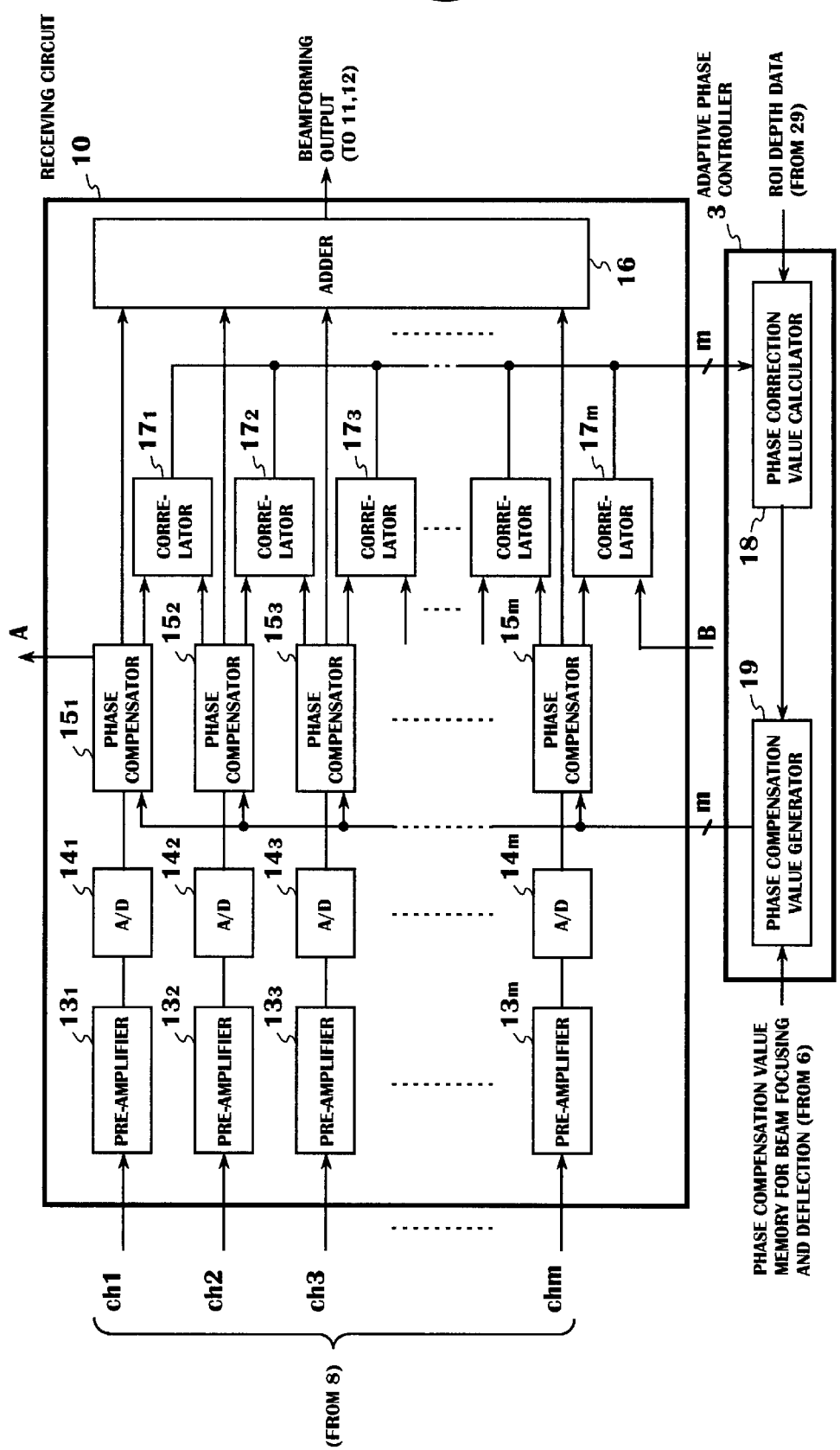
FIG. 4 is a block diagram showing the internal construction of a receiving circuit in an ultrasonic circuit unit.

Then, as shown in FIG. 4, the receiving circuit 10 is internally constructed of pre-amplifiers $13_1$ to $13_m$, A/D converters $14_1$ to $14_m$, phase compensators $15_1$ to $15_m$, an adder 16 and correlators $17_1$ to $17_m$.

The returning echo signals reflected from the diagnostic region in the object to be inspected are received by the probe 1, inversely converted into electric signals by the individual transducers and delivered, as receiving signals, to the receiving circuit 10 through the probe switching/scanning section 9 and transmission/reception separation circuit 8.

At that time, the probe switching/scanning section 9 selects m ones from N transducers so as to form an aperture for ultrasonic transmission/reception beams and concurrently, performs translation scanning such as linear scanning or convex scanning of the beams. The transmission/reception separation circuit 8 operates to efficiently transmit transmitting signal power delivered out of the transmitting circuit 7 to the probe 1 through the probe switching/scanning section 9 and protect the pre-amplifiers $13_1$ to $13_m$ (see FIG. 4) provided in the input port of the receiving circuit 10 by preventing the power from entering the receiving circuit 10 and besides, it operates to efficiently transmit reflected echo signals received by the probe 1 and supplied through the probe switching/scanning section 9 to the pre-amplifiers $13_1$ to $13_m$ of the receiving circuit 10.

Internally, the receiving circuit 10 is constructed as shown in FIG. 4. In FIG. 4, the pre-amplifiers $13_1$ to $13_m$ control and amplify individual reflected echo signals of m channels received by the probe 1 in respect of individual depths to match levels of these echo signals with the input range of the A/D converters $14_1$ to $14_m$. The aforementioned echo signals subjected to digital conversion by means of the A/D converters $14_1$ to $14_m$ are beamformed by being made to be in phase between individual channels in respect of individual depths by means of the phase compensators $15_1$ to $15_m$ which make the receiving signals of channels, having different phases for the individual transducers, be in phase in accordance with the distance to a focal point, and they are synthesized to an ultrasonic beam waveform focused to the diagnostic region by means of the adder 16. Here, the phase compensators $15_1$ to $15_m$ can utilize a circuit realized as a time delay circuit or they can be implemented by changing addresses for storing to, reading from or writing to a memory. Then, the degree of phase compensation by the phase compensators $15_1$ to $15_m$ is controlled by using a phase compensation value for beam focusing and deflection from the phase compensation value memory 6 for beam focusing and deflection shown in FIG. 3.

In the waveform of the ultrasonic beam synthesized by the adder 16, the distribution of echo signal intensities in the fundamental wave is detected and logarithmically compressed by means of the AM detection/video signal processor 11 shown in FIG. 3 so as to be delivered as a tomographic image signal of the diagnostic region and the distribution of sideband components in the fundamental wave is removed of the fundamental wave through the filter by means of the FM detection/Doppler signal processor 12 so as to detect and deliver a Doppler signal.

Then, as shown in FIG. 4, the correlators $17_1$ to $17_m$ for processing correlation between signals from the phase compensators $15_1$ to $15_m$ of individual channels are provided in the receiving circuit 10 in order to adaptively compensate the inter-channel phase difference due to sound speed irregularities in body tissues in the diagnostic region and correlation signals from the correlators $17_1$ to $17_m$ are transmitted to the adaptive phase controller 3. Phase correction value calculator 18 and phase compensation value generator 19 included in the controller control the phase compensators $15_1$ to $15_m$ by monitoring the phase difference between adjacent channels and correcting the phase compensation value for beam focusing and deflection. The adaptive phase controller 3 is connected with the phase compensation value memory 6 for beam focusing and deflection.

Figure 5:
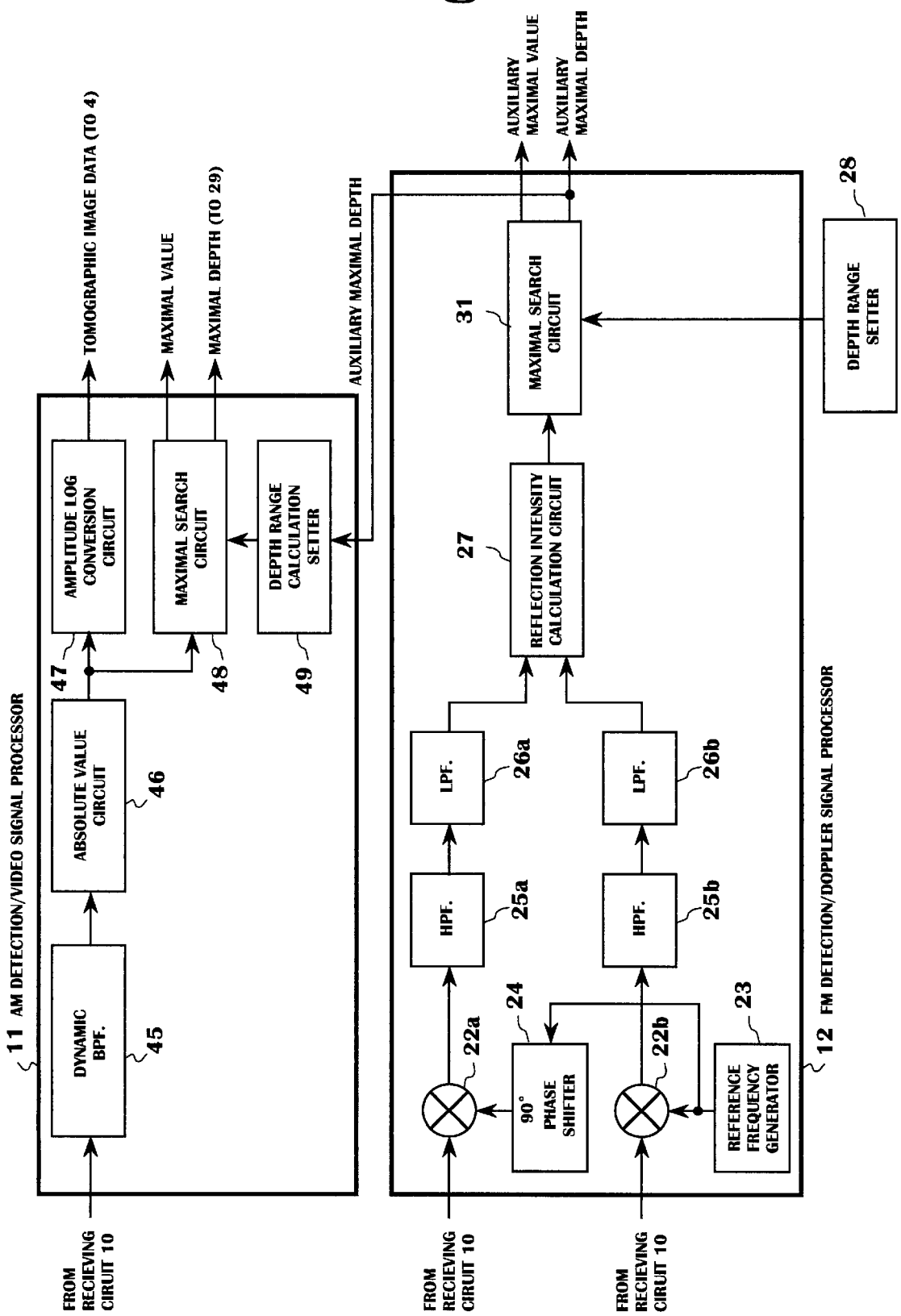
FIG. 5 is a block diagram showing the internal construction of AM detection/video signal processor and FM detection/Doppler signal processor in the ultrasonic circuit unit.

As shown in FIG. 5, the AM detection/video signal processor 11 is internally constructed of a dynamic bandpass filter (dynamic BPF) 45, an absolute value circuit 46, an amplitude LOG conversion circuit 47, a maximal search circuit 48 for searching a peak of amplitude instantaneous value and a depth range calculation setter 49 for designating a depth range in which the peak is searched. Further, as shown also in FIG. 5, the FM detection/Doppler signal processor 12 is internally constructed of multiplication circuits 22a and 22b of two systems, a reference frequency generator 23, a 90° phase shifter 24, high-pass filters (HPF's) 25a and 25b of two systems, low-pass filters (LPF's) 26a and 26b, a reflection intensity calculation circuit 27, and a maximal search circuit 31 for searching a peak of amplitude instantaneous value within the depth range set by the depth range setter 28 such as a color box setter.

The FM detection/Doppler signal processor 12 receives an input of reflected echo signal from the receiving circuit 10. The other multiplication circuit 22b multiplies a sine wave from the reference frequency generator 23 by the reflected echo signal and one multiplication circuit 22a multiplies a cosine wave 90° shifted from the reference frequency by means of the 90° phase shifter 24 by the reflected echo signal. The products are processed by the HPF's 25a and 25b and LPF's 26a and 26b of two systems, respectively, and thereafter, the reflection intensity calculation circuit 27 calculates a root of the sum of squares of respective processed products and delivers the results. As a result, the Doppler signal processor 12 removes a transmission signal frequency (principal maximal) component from the echo signal modulated by movement of the reflection (scattering) body and extracts a modulation frequency (auxiliary maximal) component forming a sideband wave of frequency spectrum. The principal maximal component is a component consisting of echoes from a stationary reflector and the auxiliary maximal component is a component consisting of echoes from a moving reflector or a scattering object in fluid.

The FM detection/Doppler signal processor 12 may be constructed as a Doppler signal detection filter generally used to detect temporal changes of flow speed at a limited region in an ultrasonic beam or to detect the two-dimensional distribution of flow speeds by scanning the ultrasonic beam.

On the other hand, the AM detection/video signal processor 11 delivers a signal representing an instantaneous absolute value of envelope of the reflected echo signal.

The DSC unit 4 writes the reflected echo signal from the ultrasonic circuit unit 2 to an internal memory in synchronism with an ultrasonic transmission/reception period and reads the written signal in synchronism with horizontal scanning in a monitor of the image display unit 5 (scanning conversion). The DSC unit includes a scan converter 20 for converting the inputted signal into an image such as an ultrasonic tomographic image or a Doppler image and a control circuit 21 for performing controlling such that the ultrasonic circuit unit 2 as a whole operates cooperatively with the operation of the DSC unit 4. Further, the image display unit 5 is adapted to display image data from the DSC unit 4 as an ultrasonic image and includes, for example, a television monitor.

Now, in the present invention, the ultrasonic circuit unit 2 is connected with the depth range setter 28 and the ROI depth data generator 29 and besides, the ROI depth data generator 29 is connected with the ROI marker generator 30 to transmit a signal to the scan converter 20. The depth range setter 28 is adapted to set a threshold value of detection level for the Doppler signal in the ultrasonic circuit unit 2 and it sets a level for detection of a Doppler signal component having intensity and speed which exceed predetermined values.

The depth range setter 28 may alternatively be constructed of a detection level setter which sets threshold values of intensity and speed to set a depth range represented by a time at which each of the levels is exceeded.

The threshold value set by the depth range setter 28 is transmitted to the maximal search circuit 31 added according to the invention in the FM detection/Doppler signal processor 12 shown in FIG. 5. The search is carried out through an operation process in which a time width around the aforementioned extracted time, which time width approximates a value corresponding to, for example, the size of a blood vessel, is set within a time range determined in advance by, for example, color box (CFM calculation range) and a maximum echo within the time range is detected on the AM detection side. In the figure, the output of the reflection intensity calculation circuit 27 has, for example, a waveform as shown at signal x(t) in FIG. 7A and the output of the depth range setter 28 has a waveform as shown at signal g(t) in FIG. 7B, so that the range covers times ts to te corresponding to the depth and time range $\Delta t$ is designated. The maximal search circuit 31 examines intensity I of x(t) in sequence, starting with the beginning (process start time) ts of the time range $\Delta t$ and ending in the deepest region (process end time) te to find a maximal value Im of intensity and delivers the value Im together with tm.

Alternatively, the depth range setter 28 may be so constructed as to deliver a threshold value It of I and the maximal search circuit 31 may be so constructed as to examine only values of intensity I at times at which x(t) exceeds It to find and deliver a maximal value Im of intensity.

The delivered tm and Im are transmitted to the AM detection/video signal processor 11 and the depth range calculation setter 49 sets a depth range represented by values around tm, for example, a time range $\Delta t'$ starting with ts' and ending in te' (FIG. 7C) and delivers a signal g'(t) resembling that in the depth range setter 28. The maximal search circuit 48 operates similarly to the maximal search circuit 31 to newly determine, in connection with an input signal x'(t), a depth (maximal depth) tim' at which the receiving signal amplitude near tm is maximized and a corresponding maximum value Im' (FIG. 7D) and transmit the determined values to the ROI depth data generator 29.

Similarly to the depth range calculation setter 49, the ROI depth data generator 29 operates to newly set process start time ts" and process end time te" around the time tm' so as to determine them to be a depth range of ROI and transmit, as shown in FIG. 4, ROI depth data to the phase correction value calculator 18 in the adaptive phase controller 3. The adaptive phase controller 3 makes a correction such that echo signals between neighboring channels exhibiting a high correlation value of the depth range are made to be in phase.

Next, in the adaptive phase controller 3 shown in FIG. 4, the phase correction value calculator 18 delivers, as a phase correction value, to the phase compensation value generator 19 a time difference between peaks of correlation between echo signals near the time corresponding to the ROI depth data from the ROI depth data generator 29. Then, the phase compensation value generator 19 corrects the phase correction value for beam focusing and deflection received from the phase correction value memory 6 for beam focusing and deflection and transmits a corrected value to the phase compensators $15_1$ to $15_m$.

The correction of phase compensation value for adaptive focusing process at a ROI region in the object to be inspected can be implemented by causing the phase compensation value generator 19 to determine phase compensation values in respect of individual ultrasonic beams in the ROI region and correcting phase compensation values for beam focusing and deflection in respect of the beams in the ROI. Alternatively, phase compensation values for beam focusing and deflection can be corrected in respect of all beams in the ROI by using a phase compensation value detected with one ultrasonic beam in the ROI. Through this, the focal point can follow the ROI region in the object to be inspected, thereby ensuring that the ultrasonic beams can be focused efficiently to the region necessary for diagnosis. After the phase compensation value for beam focusing and deflection necessary for the phase compensation of the ultrasonic scanning line in the ROI has been determined, transmission/reception of an ultrasonic wave in the same ultrasonic beam direction is again carried out. Then, beam focusing data for the transmission/reception of the ultrasonic wave at that time is based on the aforementioned corrected phase compensation value for beam focusing and deflection. In this manner, although there is a very slight time difference between the transmission/reception for determining the corrected value of the phase compensation value for beam focusing and deflection and the immediately succeeding transmission/reception, an echo signal accurately focused to only a moving reflection region can be obtained on substantially real time base.

In the present invention, the transmission/reception for obtaining the phase compensation value for beam focusing and deflection necessary for the phase compensation and the transmission/reception for image acquisition which is effected in the same transmission/reception direction immediately after the former transmission/reception by using the corrected phase compensation value for beam focusing and deflection are carried out in combination and the interior of the object to be inspected is scanned with the ultrasonic waves in a unit of the combination of these transmission/reception operations by changing the transmission/reception direction in sequence. Through this, a substantially real-time adaptive image of only a target of moving reflection region can be displayed on the television monitor of the image display unit 5.

On the other hand, the ROI marker generator 30 fetches the output signal from the ROI depth data generator 29 to generate a signal for displaying a marker at a position on image display unit 5 corresponding to the depth range of the ROI region in the object to be inspected and transmits the signal to the scan converter 20 in the DSC unit 4. Then, through the scanning conversion in the scan converter 20, an image of marker display is prepared and, as shown in FIG. 3, a ROI marker 32 is displayed at a ROI region in the display image on the image display unit 5. With the ROI marker 32, an inspector can easily confirm the ROI region in the object to be inspected from the display image on the image display unit 5. In case the ROI marker 32 need not be displayed, the ROI marker generator 30 may not always be provided.

Figure 6:
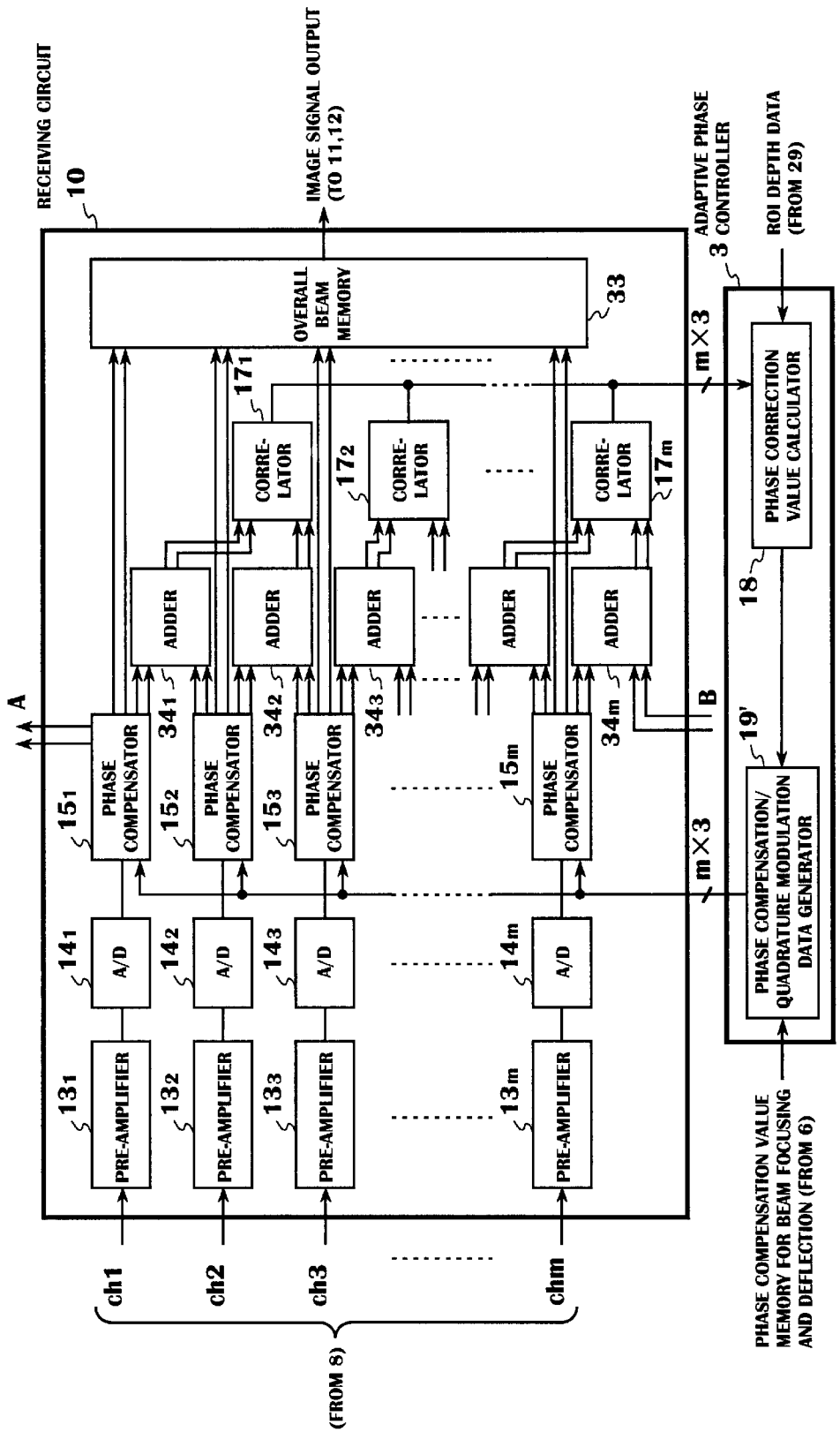
FIG. 6 is a block diagram showing another embodiment of the receiving circuit in the ultrasonic circuit unit.

FIG. 6 is a block diagram showing another embodiment of the receiving circuit 10 in the ultrasonic circuit unit 2. In this embodiment, in place of the adder 16 used for synthetic formation of one ultrasonic beam waveform focused to the diagnostic region in FIG. 4, an overall beam memory 33 is provided which generates a plurality of ultrasonic beams in a range determined by transmission/reception directional angles of transducers of the probe 1 and an inspection depth. Besides, adders $34_1$ to $34_m$ are provided to succeed phase compensators $15_1$ to $15_m$, the number of correlators $17_1$ to $17_n$ succeeding the adders is halved as compared to that in FIG. 4, and a phase compensation/quadrature modulation data generator 19' is provided in place of the phase compensation value generator 19 in the adaptive phase controller 3 shown in FIG. 4.

In the case of FIG. 6, two-system processing systems including quadrature modulation succeed the phase compensators $15_1$ to $15_m$ to store all beams, each represented by quadrature two components, in the overall beam memory 33 and a plurality of pieces of beam data are transmitted to the scan converter 20 in the DSC unit 4 shown in FIG. 3 through the AM detection/video signal processor 11 and FM detection/Doppler signal processor 12, so that the adaptive phase compensation value can be determined by using signals per se acquired within an image acquisition time of one frame and an image can be reconstructed adaptively by the same signals, thereby making it possible to perform an accurate adaptive process even in the case of a moving object to be inspected as compared to the previously-described embodiment in which images of different frames are adaptively processed. Besides, by performing the correlation process with the correlators $17_1$ to $17_n$ after the addition process with the adders $34_1$ to $34_m$, the correlation process between averages of adjacent two channels can be effected and durability against noise can be promoted.

In the foregoing description, the method of determining the phase difference between receiving signals of adjacent transducers through the correlation process is used for detection of phase correction channel in the adaptive phase controller 3 but the present invention is not limited thereto and a different method for detection of phase correction value may be used. Further, in FIG. 3, the signal of phase correction value from the adaptive phase controller 3 is transmitted to the receiving circuit 10 in the ultrasonic circuit unit 2 but by providing a signal line 35 connecting the adaptive phase controller 3 and the transmitting circuit 7 in the ultrasonic circuit unit 2 and transmitting a signal of phase correction value to the transmitting circuit 7, the adaptive focusing process can be carried out in the transmitting unit.

FIG. 8 is a block diagram showing another embodiment of the ultrasonic imaging apparatus according to the invention.

This embodiment differs from FIG. 3 in that a signal obtained by the FM detection/Doppler signal processor 12 is not supplied to the AM detection/video signal processor 11 but is supplied directly to the ROI depth data generator 29.

Operation in FIG. 8 is as follows.

Of Doppler signal components detected by the FM detection/Doppler signal processor 12, a Doppler signal component exceeding intensity and speed set by the depth range setter (detection level setter) 28 is extracted by the maximal search circuit 31 shown in FIG. 5 and a time at which the extraction is effected (auxiliary maximal depth) and a maximal value of signal level (auxiliary maximal value) are transmitted to the ROI depth data generator 29. The ROI depth data generator 29 uses the time for extraction and the maximum value of signal level to transmit, as shown in FIGS. 4 and 6, the ROI depth data for correction necessary for making echo signals of neighboring channels be in phase to the phase correction value calculator 18 in the adaptive phase controller 3. Through this, the depth for which phase control is carried out by the adaptive phase controller 3 is specified to the moving or flowing region where the Doppler signal component is detected.

According to the ultrasonic imaging apparatus of the present invention, reflected echo signals from the region in an object to be inspected where the presence of a moving internal organ or blood flow is detected are used to compensate irregularities of acoustic characteristics of body tissues in the object to be inspected so that delay data for adaptive imaging necessary to make ultrasonic waves be in phase at the detection region may be determined at adjacent transducers on the ultrasonic probe, and the ultrasonic transmission/reception is carried out by using the thus determined delay data to perform adaptive image processing, whereby by monitoring signals indicative of movement and flow in an ultrasonic beam and adaptively making receiving signals developing at the depth be in phase, focusing can automatically be made on a moving reflection region really desired to be inspected (ROI region).

Also, the delay data for adaptive imaging is determined in respect of an ultrasonic beam for a given location and immediately after transmission/reception of the above ultrasonic beam, the ultrasonic transmission/reception for the same location is effected in the same beam direction by using the determined delay data, whereby even when the wave front of a reflected echo signal from the ROI region desired to be really inspected (moving reflection region) is disturbed by the presence of irregularities of acoustic characteristics of body tissues covering the body surface of the object to be inspected and a diagnostic region in the body, focusing can automatically be made on the moving or flowing region and efficient and rapid focusing can be made on the region.

Further, the delay data for adaptive imaging is determined in respect of an ultrasonic beam for a given location and the ultrasonic transmission/reception is effected for a location adjacent to the ultrasonic beam or in the adjacent beam direction by using the determined delay data, whereby the adaptive image process can be carried out at the same frame rate without decreasing the frame rate. Accordingly, an adaptive image of a moving internal organ or blood flow can be displayed on substantially real time base by two-dimensionally scanning the transmission/reception of the ultrasonic beam in the adjacent ultrasonic scanning direction.

Furthermore, the delay data for adaptive imaging is determined in respect of all ultrasonic beams in a given frame and the ultrasonic transmission/reception is carried out in the next frame in the overall beam directions by using the determined delay data, whereby the adaptive image process can be effected every frame.

Also, the delay data for adaptive imaging is determined in respect of all ultrasonic beams in a given frame, the thus determined delay data for all ultrasonic beams is stored and the ultrasonic transmission/reception is effected every ultrasonic beam in its beam direction by using the stored delay data, whereby the adaptive image process can be effected every ultrasonic beam in respect of the beam to promote the accuracy.

Further, the ultrasonic imaging apparatus according to the present invention comprises a unit for setting a threshold value of detection level for a Doppler signal in an ultrasonic circuit, a unit for extracting a time at which the Doppler signal exceeds the set detection level and a signal level exceeding the set detection level and a unit for determining, for the phase controller, a ROI depth range for correction necessary to make echo signals of adjacent channels be in phase by using the extracted time and signal level, whereby the focal point can follow a ROI region (moving reflection region) in the object to be inspected by correcting echo signals from the region where the intensity of the Doppler signal reaches the aforementioned detection level or its neighborhood so as to make them be in phase between adjacent transducers. Accordingly, by monitoring a signal indicative of movement or flow in the ultrasonic beam and adaptively making receiving signals developing at the depth be in phase, focusing can automatically be made on the ROI region desired to be really inspected. Through this, focusing can be made on the moving or flowing ROI region in the diagnostic region and an excellent diagnostic image can be obtained.

Furthermore, by providing a unit for fetching a signal from the unit for determining the ROI depth range and generating a signal for displaying a marker at a position corresponding to the depth range on the image display unit, the marker can be displayed at the ROI region (moving reflection region) in the object to be inspected which focusing follows. Accordingly, an inspector can easily confirm the ROI region in object to be inspected in a display image on the image display unit.

What is claimed is:

1. An ultrasonic imaging apparatus comprising:
   means for transmitting ultrasonic beams in a given direction in which an internal organ in an object to be inspected or blood flows;
   means for receiving reflected echo signals affected by a Doppler effect due to the moving internal organ or the blood flow; and
   means for detecting a region in which the moving internal organ or the blood flow exists from the received reflected echo signals, so as to image the distribution of irregularities of acoustic characteristics due to body tissues in said object to be inspected and the moving internal organ or blood flow as ultrasonic images,
   wherein the reflected echo signals from the region in said object to be inspected where the presence of the moving internal organ or blood flow is detected are used to compensate irregularities of acoustic characteristics of body tissues in said object to be inspected, so that delay data for adaptive imaging necessary to make ultrasonic waves be in phase at the detection region may be determined at adjacent transducers on an ultrasonic probe, and the ultrasonic transmission/reception is carried out by using the thus determined delay data to perform adaptive image processing.

2. An ultrasonic imaging apparatus according to claim 1, wherein said delay data for adaptive imaging is determined in respect of an ultrasonic beam for a given location and immediately after transmission/reception of said ultrasonic beam, the ultrasonic transmission/reception for the same location is carried out in the same beam direction by using the thus determined delay data.

3. An ultrasonic imaging apparatus according to claim 1, wherein said delay data for adaptive imaging is determined in respect of an ultrasonic beam for a given direction and the ultrasonic transmission/reception is effected for a location adjacent to said ultrasonic beam or in the adjacent beam direction by using the thus determined delay data.

4. An ultrasonic imaging apparatus according to claim 1, wherein said delay data for adaptive imaging is determined in respect of all ultrasonic beams in a given frame and the ultrasonic transmission/reception is effected in the overall beam directions in the next a frame by using the determined delay data.

5. An ultrasonic imaging apparatus according to claim 1, wherein said delay data for adaptive imaging is determined in respect of all ultrasonic beams in a given frame, the thus determined delay data for all ultrasonic beams is stored and the ultrasonic transmission/reception is carried out for every ultrasonic beam in its beam direction by using the stored delay data.

6. An ultrasonic imaging apparatus according to claim 1, comprising means for determining delay data for adaptive imaging by using a signal for forming a sideband wave of a frequency spectrum obtained through FM detection of the received echo signal.

7. An ultrasonic imaging apparatus according to claim 1, further comprising means for further AM-detecting a signal obtained through FM detection of the received echo signal, and determining delay data for adaptive imaging by using an echo signal having the same frequency spectrum as that of the transmitting signal.

8. An ultrasonic imaging apparatus comprising:
   a probe having an array of a plurality of transducers and being operative to transmit/receive ultrasonic waves to/from an object to be inspected;
   an ultrasonic circuit unit for supplying transmitting pulses to said probe to generate ultrasonic beams, and delivering a tomographic image signal and a Doppler signal from the echo signals received by said probe;
   a phase controller for correcting the reflected echo signals in said ultrasonic circuit unit such that echo signals of neighboring channels are made to be in phase;
   a digital scan converter unit for performing scan conversion by writing and reading reflected echo signals from said ultrasonic circuit unit to and from a memory;
   an image display unit for displaying image data from said digital scan converter unit as an ultrasonic image;
   means for setting a threshold value of detection level for the Doppler signal in said ultrasonic circuit unit;
   means for extracting a time at which the Doppler signal exceeds the set detection level, and a signal level exceeding the set detection level; and
   means for determining, for said phase controller, a region of interest (ROI) depth range for correction necessary to make echo signals of neighboring channels be in phase by using said extracted time and signal level, whereby the focal point can follow the ROI in said object to be inspected by correcting echo signals from the region where the intensity of the Doppler signal reaches said detection level or its neighboring region so as to make them be in phase between adjacent transducers.

9. An ultrasonic imaging apparatus according to claim 8, comprising means for fetching a signal from said means for determining the ROI depth range, and generating a signal for displaying a marker at a position corresponding to the depth range on said image display unit, whereby the marker is displayed at the ROI in said object to be inspected which the focal point follows.

10. An ultrasonic imaging apparatus comprising:
    means for transmitting an ultrasonic wave beam into an object to be inspected;
    means for receiving echo signals including signals affected by a Doppler effect;
    means for setting a region of interest (ROI) including a portion of a moving internal organ or blood flow;
    means for retrieving a maximal signal from echo signals from said ROI;
    correlators for obtaining correlation between adjacent channels corresponding to said maximal signal;
    phase compensators for obtaining a compensation value on a basis of a correlation signal from said correlators;
    means for controlling transmission/reception of an ultrasonic wave on a basis of said compensation value; and means for creating images of said moving internal organ or blood flow from echo signals received.

11. An ultrasonic imaging apparatus according to claim 10, wherein said correlators comprise means for obtaining said correlation by measuring a time difference of peak points of said echo signals received at adjacent transducers.

12. An ultrasonic imaging apparatus according to claim 10, wherein said correlators comprise means for calculating an average correlation processing between adjacent channels.

13. An ultrasonic imaging apparatus according to claim 10, comprising means for generating depth data of said ROI on a basis of said maximal signal.

14. An ultrasonic imaging apparatus according to claim 10, wherein said phase compensators comprise means for obtaining compensation values for every scan line on a basis of correlation signals from said correlators.

15. A method of producing ultrasonic images, comprising:

executing a first transmission/reception operation of an ultrasonic wave for obtaining compensation values for compensation of beam focusing;

obtaining a depth range of a region of interest (ROI) on a basis of peak points of echo signals;

obtaining compensation values for compensation of beam focusing on a basis of said depth range;

executing a second transmission/reception operation of an ultrasonic wave compensated with said compensation values; and producing tomographic images on a basis of echo signals received in said second transmission/reception operation of the ultrasonic wave.

16. A method of producing ultrasonic images according to claim 15, wherein said obtaining a depth range of a ROI comprises:

retrieving a peak point of reflection intensity of echo signals in a first time period corresponding to a predetermined depth range;

setting a second time period narrower than said first time period so as to include a peak point of echo signals in said first time period; and setting said depth range of a ROI on a basis of said second time period.

17. A method of producing ultrasonic images according to claim 15, comprising displaying a marker representing said depth range of said ROI on an image displayed.

* * * * *